US009739718B2

(12) United States Patent
Woolley et al.

(10) Patent No.: US 9,739,718 B2
(45) Date of Patent: Aug. 22, 2017

(54) FLOW-VALVE DIAGNOSTIC MICROFLUIDIC SYSTEM

(71) Applicants: Adam T. Woolley, Orem, UT (US); Debolina Chatterjee, Provo, UT (US); Danielle Scarlet Mansfield, Mapleton, UT (US)

(72) Inventors: Adam T. Woolley, Orem, UT (US); Debolina Chatterjee, Provo, UT (US); Danielle Scarlet Mansfield, Mapleton, UT (US)

(73) Assignee: Brigham Young University, Provo, UT (US)

( * ) Notice: Subject to any disclaimer, the term of this patent is extended or adjusted under 35 U.S.C. 154(b) by 740 days.

(21) Appl. No.: 14/170,941

(22) Filed: Feb. 3, 2014

(65) Prior Publication Data

US 2014/0308754 A1 Oct. 16, 2014

Related U.S. Application Data

(63) Continuation of application No. PCT/IB2012/002103, filed on Aug. 3, 2012.

(60) Provisional application No. 61/574,554, filed on Aug. 4, 2011.

(51) Int. Cl.
*G01N 21/78* (2006.01)
*G01N 33/543* (2006.01)
*B01L 3/00* (2006.01)

(52) U.S. Cl.
CPC ........ *G01N 21/78* (2013.01); *B01L 3/502746* (2013.01); *G01N 33/54366* (2013.01); *B01L 2400/0672* (2013.01); *B01L 2400/084* (2013.01)

(58) Field of Classification Search
None
See application file for complete search history.

(56) References Cited

U.S. PATENT DOCUMENTS

| | | | |
|---|---|---|---|
| 6,395,557 B1 * | 5/2002 | Fouillet | G01N 33/54366 422/68.1 |
| 7,863,035 B2 | 1/2011 | Clemens | |
| 2005/0009101 A1 | 1/2005 | Blackburn | |
| 2009/0079963 A1 * | 3/2009 | Ermantraut | B01F 11/0045 356/39 |
| 2010/0179068 A1 * | 7/2010 | Kaiser | B01L 3/502715 506/9 |
| 2012/0186977 A1 * | 7/2012 | Sjong | B01L 3/502707 204/451 |

OTHER PUBLICATIONS

Thorslund (2007) Sens Actuat 123:847-855.*
Yu (2009) Lab Chip 9: 1243-1247.*
Chin (2011) Nature Medicine 17: 1015-1020.*
(Continued)

*Primary Examiner* — Melanie Y Brown
*Assistant Examiner* — Richard Moerschell
(74) *Attorney, Agent, or Firm* — James Sonntag

(57) ABSTRACT

A system for detecting concentration of a target in a solution where sample fluid is passed into a microchannel with wall coated with the receptor that reacts and crosslinks with the target to constrict the channel and slow or stop sample flow through the microchannel. Concentration of the target is determined by measuring length of the sample filled channel.

19 Claims, 6 Drawing Sheets

(56) References Cited

OTHER PUBLICATIONS

Yu et al., Lab on a Chip, 2009, vol. 9, No. 9, pp. 1243-1247.
Chin et al., Nature Medicine, Jul. 31, 2011, vol. 17, No. 8, pp. 1015-1020.
Thorslund et al., Sensors and Actuators B, 2007, vol. 123, No. 2, pp. 847-855.
Written Opinion of the International Searching Authority, PCT/IB2012/002103, Mar. 18, 2013.

\* cited by examiner

FLOW-VALVE DIAGNOSTIC MICROFLUIDIC SYSTEM

CROSS REFERENCE TO RELATED APPLICATIONS

This application is a continuation from International Application under the Patent Cooperation Treaty PCT/US2012/049640 (PCT/IB2012/002103), filed 3 Aug. 2012, which claimed priority from U.S. Provisional Patent Application 61/574,554 filed 4 Aug. 2011, which applications are hereby incorporated by reference.

FEDERAL SUPPORT

This invention was made with government support under Grant Number EB006124 by the National Institutes of Health. The government has certain rights in the invention.

BACKGROUND

Advanced analysis systems have a number of important desired performance characteristics, namely accuracy, reliability, selectivity for target analytes, quantitation, low detection limits, simplicity, speed, cost, multiplexing, and so on. Frequently, there is a tradeoff between these objectives (e.g., low cost vs. high accuracy), requiring a compromise that best meets the analysis requirements. For example, the performance of benchtop analyzers takes precedence over portability, while for point-of-care (POC) systems, versatility and performance are often sacrificed in favor of convenience.

A number of automated and robust laboratory-based systems are available for analyses. Liquid chromatography[1] is widely used and has seen recent progress in stationary phases[2, 3] and with increased pressures.[4] Mass spectrometry methods[5, 6] have advanced through improved mass analyzers[7] and sample introduction techniques.[8] Spectroscopy can provide analyte-specific information from absorbance[9] or Raman[10] techniques. In addition, clinical diagnostic tools[11] such as enzyme-linked immunosorbent assay (ELISA)[12] are broadly used for targeted detection of biomolecules of interest. The above examples nicely illustrate systems with excellent performance, but that capability generally comes at the expense of portability.

On the other hand, portable instruments offer significantly increased analysis convenience. For example, POC diagnostic devices have been implemented in monitoring blood glucose for diabetes[13] and in home pregnancy testing.[14] Paper-based microfluidic systems[15-17] offer simplified analysis coupled with low cost. These portable systems are advantageous in terms of simplicity and speed, but this generally comes at the cost of some performance characteristics such as low detection limits, quantitation capabilities, or multiplexing.

SUMMARY

An aspect is a simple-to-use, portable and detectorless microdevice system with quantitation capabilities, ~1 ng/mL detection limits and potential for broad applicability, addressing key limitations of both benchtop and portable systems.

Other aspects are simplified analysis systems that offer the performance of benchtop instruments but the convenience and portability are highly desirable. Novel, miniature devices have been developed that feature visual inspection readout of a target's concentration from a ~1 µL volume of solution introduced into a microfluidic channel. Microchannels are constructed within an elastomeric or deformable material, and channel surfaces are coated with receptors to the target. When a solution is flowed into the channel, the target crosslinks multiple receptors on the surface, resulting in constriction of the first few millimeters of the channel and stopping of flow. Quantitation is performed by measuring the distance traveled by the target solution in the channel before flow stops. A key advantage of this approach is that quantification is accomplished by simple visual inspection of the channel, without the need for complex detection instrumentation.

These devices have been tested using the model system of biotin as a receptor and streptavidin as the target. Three factors have been tested that influence flow distance: solution viscosity, device material thickness, and channel height and geometry. It has been found that solution capillary flow distance scales with the negative logarithm of target concentration and streptavidin concentrations as low as 1 ng/mL have been detected. Finally, a plausible mechanism has been identified and evaluated wherein time-dependent channel constriction in the first few millimeters leads to concentration-dependent flow distances. Their simplicity coupled with performance makes these "flow valve" systems especially attractive for a host of analysis applications.

In an aspect a microchannel is a deformable material coated with receptor molecules. This acts as a self-constricting valve due to binding of receptor and target molecules. When a sample containing target molecules flows through the receptor-coated microchannel, the binding force between target and receptor causes the microchannel to constrict and prevent or markedly slow fluid from flowing further in the channel. This flow stoppage can be detected by the naked eye because the refractive indices of air in an empty microchannel and fluid in a filled microchannel are sufficiently different that it is easy to distinguish the empty portion of a microchannel from the filled portion of a microchannel.

One of the great advantages of flow valve diagnostics is that it is a quantitative point-of-care (POC) technique. Tests using the model target/receptor system of streptavidin-biotin indicate that there is a linear relationship between flow distance (i.e. how far the sample flowed in the microchannel before valve constriction prevented further flow) and $\log_{10}$ [target]. Therefore, the flow distance can be measured and used to ascertain the target concentration in a sample. As there are few simple, inexpensive, and quantitative POC methods, flow valve diagnostics has the potential to meet a specific need in the realm of POC testing.

The first or inlet end of the microchannel is deformable to allow for the closure. "Deformability" is affected by the materials in which the microchannels are formed, the thickness of the material over the microchannel, and the geometry of the microchannel cross-section.

The material in which the microchannels are formed must be sufficiently deformable to allow deformation and constriction of the channel to close or provide dependent flow valve effect under binding forces of the surface receptor and solution target reaction. Elastomeric materials are suitable and include, but are not limited to, polydimethylsiloxane (PDMS), poly-(polyethylene glycol diacrylate), fluoroelastomers, polyfluoropolyethers, such as polyfluoropolyether diol methacrylate, Viton™, Dyneon THV™, Fluorolink™ and thermoset polyester.

The microchip thickness is suitable for structural integrity of the chip. The thickness of the material above the channel affects channel constriction for the flow valve function. In conventional fabrication techniques this is the thickness of the top layer over a substrate containing the microchannel. The smaller this thickness, the easier it is for the material to flex and constrict. Using PDMS a thickness of 0.45 to 0.5 mm has been found sufficient. Smaller thicknesses are possible, but are difficult to work with. Silicone films may allow for less thickness.

The geometry of the microchannel cross-section is important. Rectangular cross-section microchannels don't seem to allow sufficient deformation of the channel to close it. It has been shown the "semicircular" or curved channels having a straight bottom edge and an arced top in the general shape of a semicircle, or a portion of a semicircle is suitable. This cross-section can be easily provided by reflowing the photoresist during mold fabrication, as further described below. Reflowing, or heating the photoresist to a temperature above its melting point after exposure and development, changes the microchannel geometry from rectangular to semicircular.

Basically, the channel must be able to deform and close. It is believed that an effective closure occurs when the surface receptors react with the solution targets forming a cross-linked coating that grows on nearby surfaces to join and draw the surfaces together by deforming the channel. This requires that the channel height at certain regions be on a molecular scale. This can occur at surfaces regions near the acute angles in a semicircular pattern, where the surfaces are close enough to be drawn together. This then brings adjacent surfaces closer together, enough to also be deformed and pulled together by receptor-target linkages. This process continues until fluid closure. Any geometric shape of the channel cross-section that permits this process is contemplated.

Other geometries are suitable, but may require other techniques in molding and fluid microchip fabrication for their formation. Suitable geometries are those that can functionally operate as a closing valve by interaction of the receptors with the targets. It is believed that geometries that depart from rectangular and approach or include features of the semicircular geometry are suitable, such as shapes where the height increases smoothly from 0 at one side to a maximum near the center and then decreases back to 0 at the other side. Geometries with facing acute angles joined by straight lines or curved lines are believed to be suitable. The curved lines may include straight-line segments joined by obtuse or flat angles. Examples of contemplated geometries include, shapes with one, two or more acute angles, rectilinear and curvilinear shapes, semicircles or eye-shapes from straight lines and circle segments that are semicircular or less, flat isosceles triangles, trapezoids, or other like flattened polygonal shapes, and lenticular or lens-shapes.

The closure of the channel results from molecular interactions can cause deflections that are of a much larger, micrometer scale. While not being bound to any theory, it is believed that at the edges of the microchannels, at regions where surfaces meet and closely oppose each other the channel height is at or near a molecular scale (about 10 nm) such that crosslinking between the two surfaces is possible. This interaction pulls the surfaces incrementally closer, enabling similar molecular-scale crosslinking to occur moving inward toward the middle of the channel. As this interaction progresses, the edges of the channel become deformed and constricted until fluid flow is not possible or is reduced to provide a dependent valve flow effect.

"Closure" or "stoppage" as use herein and in the claims is defined as the point when flow of fluid through the microchannel ceases, or has no or insignificant movement. Thus, flow may not be literally stopped, but slowed. It is contemplated that the flow is stopped or slowed sufficiently to provide a concentration flow valve effect.

Concentration flow valve effect can be defined as the target-mediated crosslinking of receptors on the top and bottom surfaces of a microchannel making the capillary flow distance of solution depend on target concentration. This is the distance a sample solution flows along a microchannel before it is stopped or significantly slows, which proportional to the concentration of the target in the solution. It has also been found that in certain systems where the fluid flow is not fully stopped, the rate of flow becomes proportional to the concentration. Accordingly, measuring the flow distance at a given time can also be used to quantify the concentration.

The dimensions of the microchannel are any suitable that allow the microdevice to function as described. Suitable heights include between 1 and 50 microns, or 5 and 20 microns. Suitable lengths of the channel include those between 10 and 1000 mm, or 20 and 200 mm. Where PDMS is used the thickness of the top cover, or the thickness above the channel is suitably between 0.4 and 1.0 mm.

The closure of the microchannel occurs at the first or inlet end of the channel. Accordingly, the coating of microchannel wall with receptors and the shape of the cross-section are only critical at the first inlet end. It is contemplated to construct the microchannel with uniform or non-uniform cross-section, and with a coating for all or a portion of its length, as long as the inlet of microchannel is constructed with the requirements (1) cross-sectional shape that will deform and close and (2) sufficient receptor sites at the inlet that when reacted with targets in solution will deform and close the channel at a rate in proportion to the concentration of targets in the solution.

The remaining portion of the microchannel not corresponding to the deformable inlet can be of any suitable cross-section, and may or may not be coated with receptors. The length of the channel is sufficient such the fluid will not flow the entire length of the channel before closure at the lower detection limits of the device.

Since concentration of the target is determined by observation of the distance the fluid flows down the microchannel a microchannel, a pattern that enables such should be used. This includes straight channels, or serpentine channels in a uniform rectangular pattern. Other patterns are contemplated. In addition, the material of the device should be of a transparency and refractive index to show contrast between a fluid filled microchannel and an air or filled or empty microchannel. The structure or measurement scale or calibration markings used to measure the distance can be any suitable construction. For example, a "ruler" scale can be one or more micropatterned calibration markings made into the device during fabrication (See FIG. 2-A at 2 cm.), or a scale with a pattern can be adhered or mounted near or behind the channel. (See FIG. 2-A.)

The distance that the solution flows down the microchannel is proportional to the negative logarithm of the concentration of the target in the solution. According, a device can be calibrated, for example, with a standard, and devices constructed the same can be used to measure directly unknown target concentration in a sample by measuring the distance of fluid travel down the microchannel.

The device is made using standard micromachining techniques, including, but not limited to, techniques including one or more of photolithography, replica molding, and plasma oxidation.

Viscosity of the samples to be tested may be considered in the microchannel lengths and construction. Viscous sample liquids flow more slowly under capillary action, providing more time for the receptors and targets to cross-link and narrow the channel. Viscosity modifiers to increase the viscosity, such as glycerol, may be added to the samples. A useful viscosity range has been found to be between 1.0 and 4.0 cP.

The receptors are any one or more of molecules that bond to a target molecule to be detected. In addition, the receptor/target reaction must form a cross-linked product to bind, deform, and constrict the channels. In general, receptors must recognize at least two distinct sites on the target for crosslinking. Suitable receptor/target systems include antibody/antigen, certain appropriately designed nucleic acid oligomers, receptors such as streptavidin-biotin, anti-streptavidin (receptor) and streptavidin (target). The requirement is that the receptor can be coated on the microchannel wall, and that it reacts with a target in a sample solution. More than one receptor-target system may be used. Antibody systems may include monoclonal or polyclonal antibodies. For example two monoclonal antibodies that bind to different epitopes or a polyclonal antibody receptor that binds with multiple epitopes of the same antigen are contemplated. Also two different nucleic acid sequences (receptor) that recognize different parts of a single nucleic acid target sequence are contemplated.

DETAILED DESCRIPTION

Example I

Figure 1:
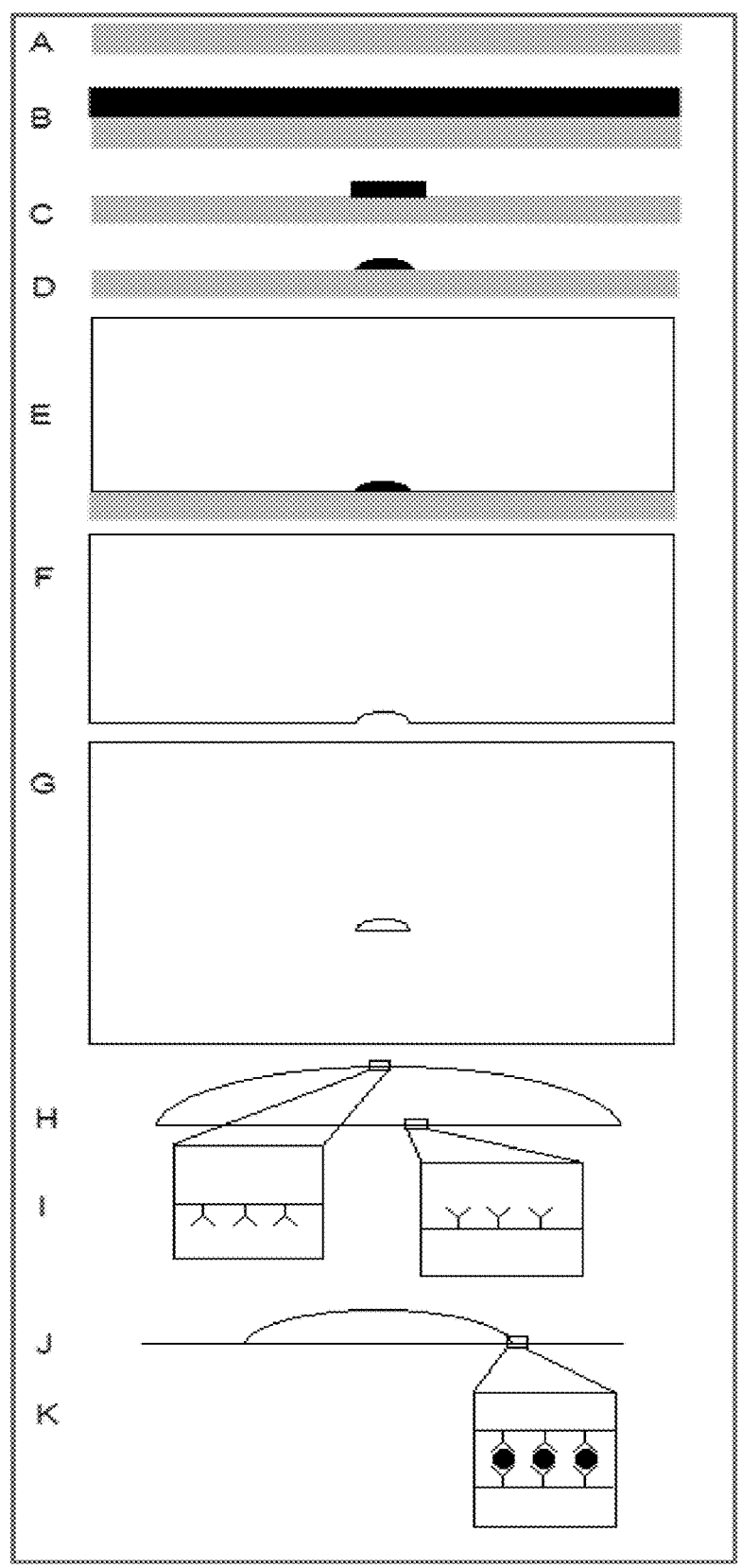
FIG. 1. Flow valve device fabrication and channel closure process. Microchannel and PDMS layer dimensions are not shown at scale. (A) Glass wafer (gray). (B) AZ50XT positive photoresist (black) spun on wafer. (C) Photolithographic patterning to form a mold with elevated feature using UV exposure and development with AZ400K developer. (D) Reflowing of photoresist at 150° C. for 5 min to yield a curved feature. (E) PDMS cured (80° C., 45 min) on mold. (F) Cured PDMS released. (G) Plasma bonding to enclose the microchannel. (H) Cross section zoom view of the open channel in (G), coated with receptors. (I) Zoom view (~1000×) of the boxes in (H), showing receptors on the top and the bottom channel walls. (J) Cross section of a partially closed channel. (K) Zoom view (~1000×) of the box in (J), showing receptor-target interaction leading to channel closure.

Immediately after plasma bonding and oxidation, the microchannels of the flow valve devices were filled with biotinylated-bovine serum album (biotinylated-BSA, Thermo Scientific, Rockford, Ill., 2 mg/mL in 0.14 mM citrate buffer, pH 6.8) by capillary action. The biotinylated-BSA was allowed to adsorb to the channel walls for 15 min. After that time period, unadsorbed biotinylated-BSA was flushed from the channel using phosphate buffered saline (PBS, 10 mM, pH 7.2). Last, PBS was removed from the channel and 1 μL of streptavidin solution (New England Biolabs, Ipswich, Mass.) of known concentration in PBS was pipetted into the reservoir. Flow distance was recorded with a ruler and images were obtained with a digital camera.

Results indicated that $\log_{10}$ [streptavidin] and flow distance share a linear relationship. Therefore, for a given device design, one is able to create a standard curve and subsequently determine the concentration of unknown samples by measuring flow distance.

An aspect is a method that involves the capillary flow of target solution through a receptor-coated microchannel in a deformable material, which leads to channel constriction and flow stoppage due to target-receptor interaction. Importantly, in this "flow-valve" method, the distance of capillary flow is correlated with the target's concentration, and the ability to differentiate between filled and empty channels visually enables detectorless determination of flow distance, and hence target concentration. Polydimethylsiloxane (PDMS) devices have been fabricated and tested them with the model target-receptor system of streptavidin and biotin. Furthermore, three factors were studied that affect assay performance: solution viscosity, device material thickness and channel height. The concentration dependence of flow distance and assayed streptavidin solutions as dilute as 1 ng/mL has been measured. Finally, the mechanism of channel closure in these assays was evaluated. Notably, the "flow valve" approach should be adaptable to various target-receptor pairs, offering a very broadly applicable analysis method.

Experimental Section

Mold Design and Preparation.

Molds were prepared using a 500 μm thickness, 10 cm diameter glass wafer (FIG. 1A) with spun on AZ50XT positive photoresist (AZ Electronic Materials, Branchburg, N.J.) of 5-20 μm thickness (FIG. 1B). Next, photolithography was used to transfer the serpentine design of the mask (FIG. 2A) onto the glass wafer by UV exposure followed by development in AZ400K developer (AZ Electronic Materials), resulting in elevated features of 50 μm width on the wafer (FIG. 1C). Reflowing of photoresist[19] was then done at 150° C. for 5 min to round the edges of the elevated features in the mold (FIG. 1D).

PDMS Device Fabrication.

Devices were fabricated by casting PDMS against the positive relief mold. PDMS (Dow Corning, Centennial, Colo.) was prepared by mixing the base and curing agent in a 10:1 ratio, pouring it on the mold to a thickness of 0.45-1.1 mm (FIG. 1E), and heating to 80° C. for 45 min for curing. This PDMS was removed from the mold (FIG. 1F) and bonded to an unpatterned PDMS layer (thickness: 0.4-1.1 mm) after exposure to an oxygen plasma for 30 s[20] to form a completed device with embedded channel (FIG. 1G). After plasma bonding, devices were stored with water in the channels to ensure that the surface remained hydrophilic.

Procedure for Experimentation.

Experiments were carried out on a biotin-streptavidin model system using the general protocols given here. The water-filled microchannel was first aspirated and then filled with biotinylated bovine serum albumin (b-BSA, Thermo Scientific, Rockford, Ill., 2 mg/mL in 0.14 mM citrate, pH 6.8) or a control solution of BSA (Sigma-Aldrich, St. Louis, Mo., 2 mg/mL in phosphate buffered saline) via capillary action. The b-BSA was allowed to adsorb to the PDMS channel walls for 15 min, leaving exposed biotin groups. Then, the b-BSA solution was removed and the channel was flushed with phosphate buffered saline (PBS, 10 mM, pH 7.2) to remove unadsorbed material. Finally, PBS was aspirated from the channel and a 1 μL streptavidin solution (New England Biolabs, Ipswich, Mass.) of specified concentration in PBS was pipetted into the reservoir (see FIG. 2C-D). The flow distance of streptavidin solution in the microchannel was measured with a ruler, and photographs were obtained with a digital camera. Some flow experiments were also carried out with streptavidin solutions having added glycerol (0-36%) to explore the influence of viscosity.

Flow Restriction Mechanism.

Fluorescein sodium salt (80 ng/mL, Spectrum, Gardena, Calif.) in PBS was mixed with unlabeled streptavidin or BSA as a control (both 500 μg/mL in PBS) and allowed to flow in 13 μm tall biotin-modified microchannels. Fluorescence signal was monitored using a CCD camera (CoolSNAP HQ2, Photometrics, Tucson, Ariz.) attached to an upright microscope (Axio Scope, A1, Zeiss, Thornwood, N.Y.). Illumination was provided by a 625 mW LED (MBLED, Thorlabs, Newton, N.J.) that passed through a filter cube (FITC-LP01-Clinical-OMF, Semrock, Rochester, N.Y.). Images were acquired using a 400 ms exposure time. Image acquisition and data analysis were performed using Image J software. The fluorescence signal from fluorescein in these images, integrated across the channel at different flow distances, was obtained. From these traces, background subtracted, normalized channel fluorescence signal peak areas (proportional to channel cross sectional areas) were obtained for flow solutions containing either streptavidin or BSA (control).

Contact angles of streptavidin solution droplets of different concentrations on biotinylated PDMS substrates were measured using a contact angle goniometer (Rame-Hart, Succasunna, N.J.).

Results and Discussion

Figure 2:
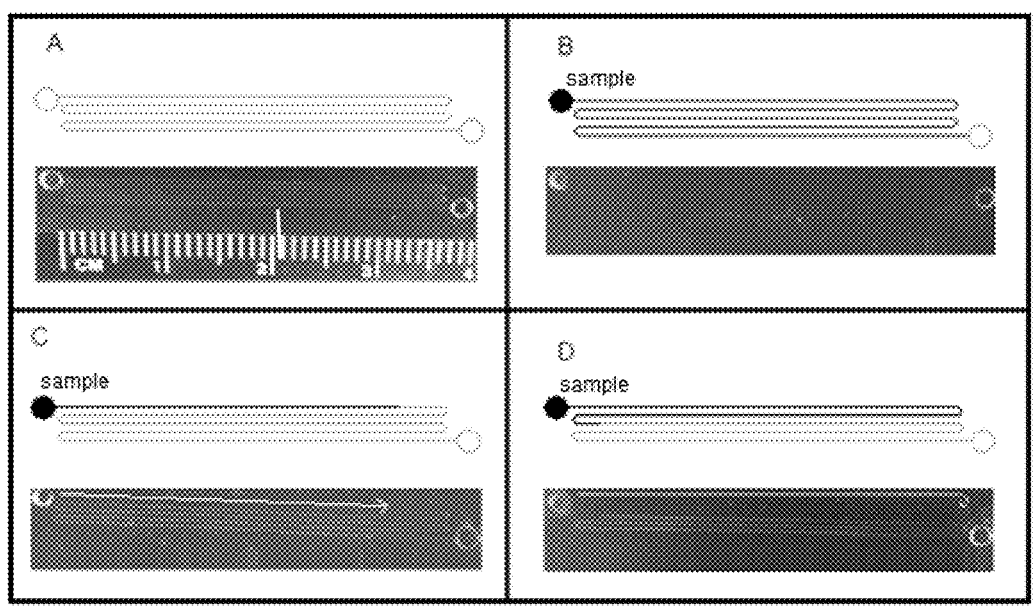
FIG. 2. Flow-valve assay concept and data, with device schematic (top) and photograph (bottom) in each panel. Devices had biotinylated-BSA coated channels 17 μm tall and 58 μm wide, and a PDMS cover layer thickness of 0.5 mm. White arrows indicate direction of flow. (A) Open and empty channel, visible as no solution is in it. (B) Channel filled with solution lacking streptavidin, which travels the entire length of the channel without stopping, making the channel difficult to distinguish from the surrounding device. (C) 32 mm flow distance for 10 μg/mL streptavidin solution loaded in the channel. (D) 83 mm flow distance for 100 ng/mL streptavidin solution added to the channel.

Experiments on a model system, biotin-streptavidin, were conducted to test the devices and enable their optimization. Studied were the effects on flow distance of channel height and shape, PDMS cover layer thickness, and solution viscosity. The mechanism through which channel closure affects flow was also probed. FIG. 2 shows a few examples of the data resulting from "flow valve" assays. Unfilled flow channels are easily seen in the photographs (e.g., FIG. 2A), and similarly under simple visual inspection. In contrast, microchannels containing liquid, as demonstrated in FIG. 2B, are no longer seen readily.

Initial experiments were conducted on 35 mm long, 58 μm wide channels with a 1.1 mm thick PDMS cover layer. Channels with a height <5 μM usually became blocked by the flow of only water or during coating with b-BSA, either because of channel deformation due to capillary forces or due to surface crosslinking during BSA adsorption. In a revised device design with slightly taller microchannels (5.2 μm) and a PDMS cover layer thickness of 0.7 mm, a 1.0 mg/mL streptavidin solution traveled 10 mm, and a 0.88 mg/mL streptavidin solution traveled 15 mm, while solutions lacking streptavidin flowed the full length (35 mm) of the b-BSA coated channel. When glycerol was added to a 28% concentration, a solution with a streptavidin concentration of 60 μg/mL flowed 30 mm in a 5.2 μm tall channel with a 0.7 mm PDMS cover layer thickness. These experiments identified three assay parameters (channel height, cover layer thickness and solution viscosity) that could be altered to affect the dynamic range and limit of detection for "flow valve" experiments. Reproducible results for these initial device designs were still somewhat difficult to obtain, which was attributed to the above-noted blockage issues associated with relatively shallow channels.

A curved channel cross-section (FIG. 1G) was found suitable for channel constriction, probably because pinching shut from the sides towards the center was possible with this geometry (see FIG. 1H-J). Flow experiments were done with curved and rectangular cross-section channels coated with biotin (both 58 μm wide and 5.2 μm tall with a 0.7 mm PDMS top layer thickness); 1.0 mg/mL streptavidin solution flowed only 10 mm in the curved cross-section channel before flow stopped, but the same solution flowed the full length of the rectangular cross-section channel. The results with this channel geometry are also consistent with published work showing that a curved channel is easier to close than a rectangular channel for valves actuated by external pressure.[21]

Building on these initial studies, Further characterization was made of the three factors that affected channel closure: solution viscosity, PDMS cover layer thickness and channel height. One parameter was varied while holding others constant and observed any effects on the flow distance. Also, taller (13-17 μm) channels were used to avoid some of the issues previously seen with shallower ones. When a higher streptavidin concentration (10 μg/mL) was introduced into a biotin-modified channel (FIG. 2C), more rapid cross-linking of the biotin anchored to the surface in the first few millimeters of the channel length led to faster constriction at the start of the channel and a shorter capillary flow distance traveled by the streptavidin solution. On the other hand, when a lower concentration of streptavidin solution (100 ng/mL) was loaded (FIG. 2D), slower cross-linking led to a greater capillary flow distance for the streptavidin solution before constriction in the first few millimeters of the channel stopped flow. A more in-depth discussion of this hypothesized mechanism of channel closure and flow stoppage is provided later.

Figure 3:
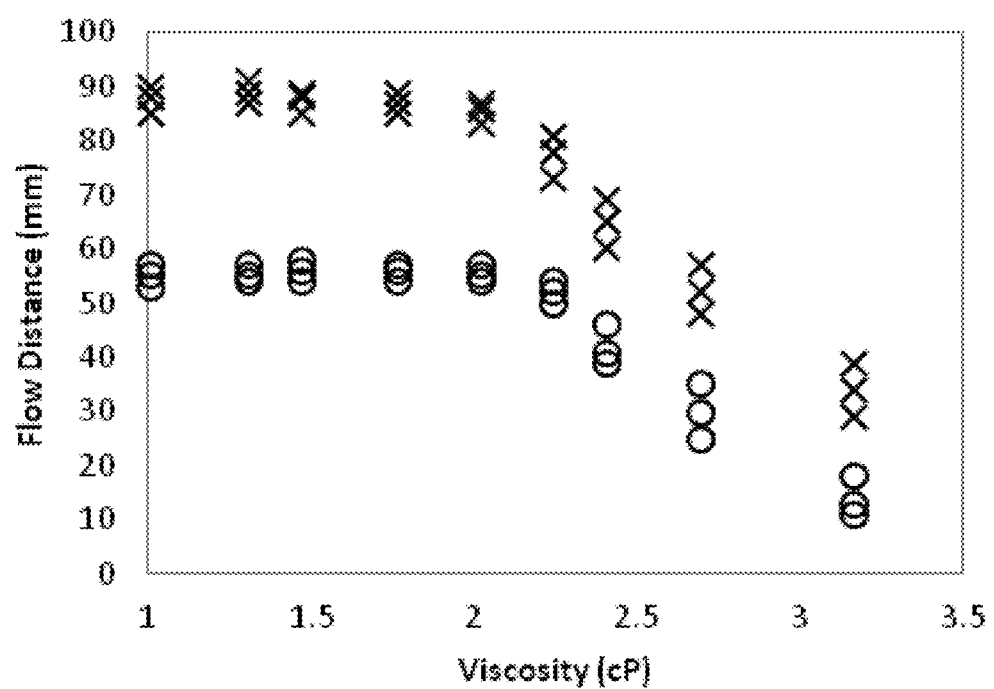
FIG. 3. Effect of solution viscosity on the flow distance of 100 ng/mL (X) and 1.0 μg/mL (○) streptavidin solutions in biotin-modified 17 μm deep and 58 μm wide channels with a 0.5 mm PDMS top layer. Flow distance is only affected above a threshold viscosity of ~2 cP, corresponding to 24% glycerol.

The effect of solution viscosity on the flow distance was studied with other variables held constant. Added glycerol adjusted the solution viscosity, and control solutions containing glycerol but lacking streptavidin flowed the entire length of the microchannels. FIG. 3 shows the effects of solution viscosity (1.0-3.2 cP, corresponding to glycerol concentrations of 0-36%)[22] on flow distance for 100 ng/mL and 1.0 µg/mL streptavidin. There was little effect on the flow distance for viscosities less than ~2 cP (24% glycerol), but with further increases in viscosity, the flow distance decreased. Below 2 cP, the solution viscosity also had little effect on flow velocity (10-12 s to flow 80 mm, with or without glycerol). However, above 2 cP, the solution viscosity led to slower solution flow through the channel that increased the time for biotin-streptavidin interaction and closure of the first few millimeters of the channel. Thus, the distance solution traveled before channel constriction restricted flow was shorter for both concentrations of streptavidin. The 100 ng/mL solutions travelled a greater distance than the 1.0 µg/mL ones, in line with expectations. It was further found that added glycerol could be used to adjust the linear range for detection for a given microchannel length, although adding glycerol increased the assay complexity compared to flowing solution without viscosity adjustment. Indeed, flow experiments done in duplicate in glycerol-adjusted 3.0 cP solutions in 17 µm b-BSA coated channels yielded the following results: control solutions lacking streptavidin flowed 95 and 100 mm; solutions containing 1 ng/mL streptavidin flowed 56 mm and 67 mm; and 100 pg/mL streptavidin solutions (a factor of 10 lower concentration than this laboratory has been able to detect reliably in 1.0 cP buffer solutions) flowed 71 mm and 84 mm. It is also valuable to understand the viscosity dependence of flow distance in these devices for possible future work with viscous samples like blood.

Figure 4:
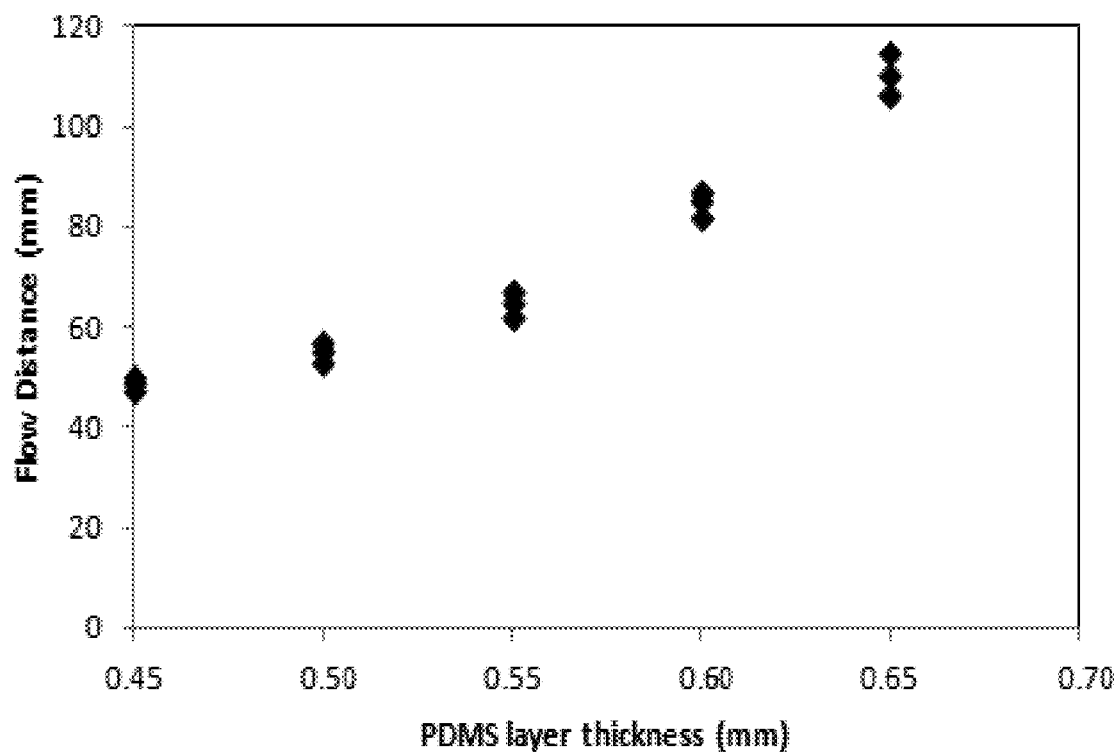
FIG. 4. Effect of PDMS layer thickness on the flow distance for 1.0 μg/mL streptavidin in biotin-modified 17 μm deep and 58 μm wide channels. Flow distance decreases asymptotically as PDMS layer thickness is reduced.

The effect of PDMS cover layer thickness on the flow distance was also studied with all other parameters held constant. FIG. 4 shows the influence of different PDMS top layer thicknesses on the flow distance for 1.0 µg/mL streptavidin in biotin-modified channels. The flow distance decreases at a slower rate as PDMS layer thickness is reduced, approaching an asymptote around 0.45 mm cover layer thickness. The shorter flow distances are attributed for thinner cover layers to the reduced force needed to deflect the cover layer and constrict the first few millimeters of the channel, resulting in more rapid constriction and hence shorter capillary flow time and distance. The leveling off observed approaching 0.45 mm thickness may occur because forces exerted in the channel by capillary flow itself become the dominant process in channel constriction at these shallower depths, leading to similar flow times and distances. From the data obtained, it was concluded that cover thickness allows control of the flow distance, and thus this parameter can adjust dynamic range or limit of detection.

Figure 5:
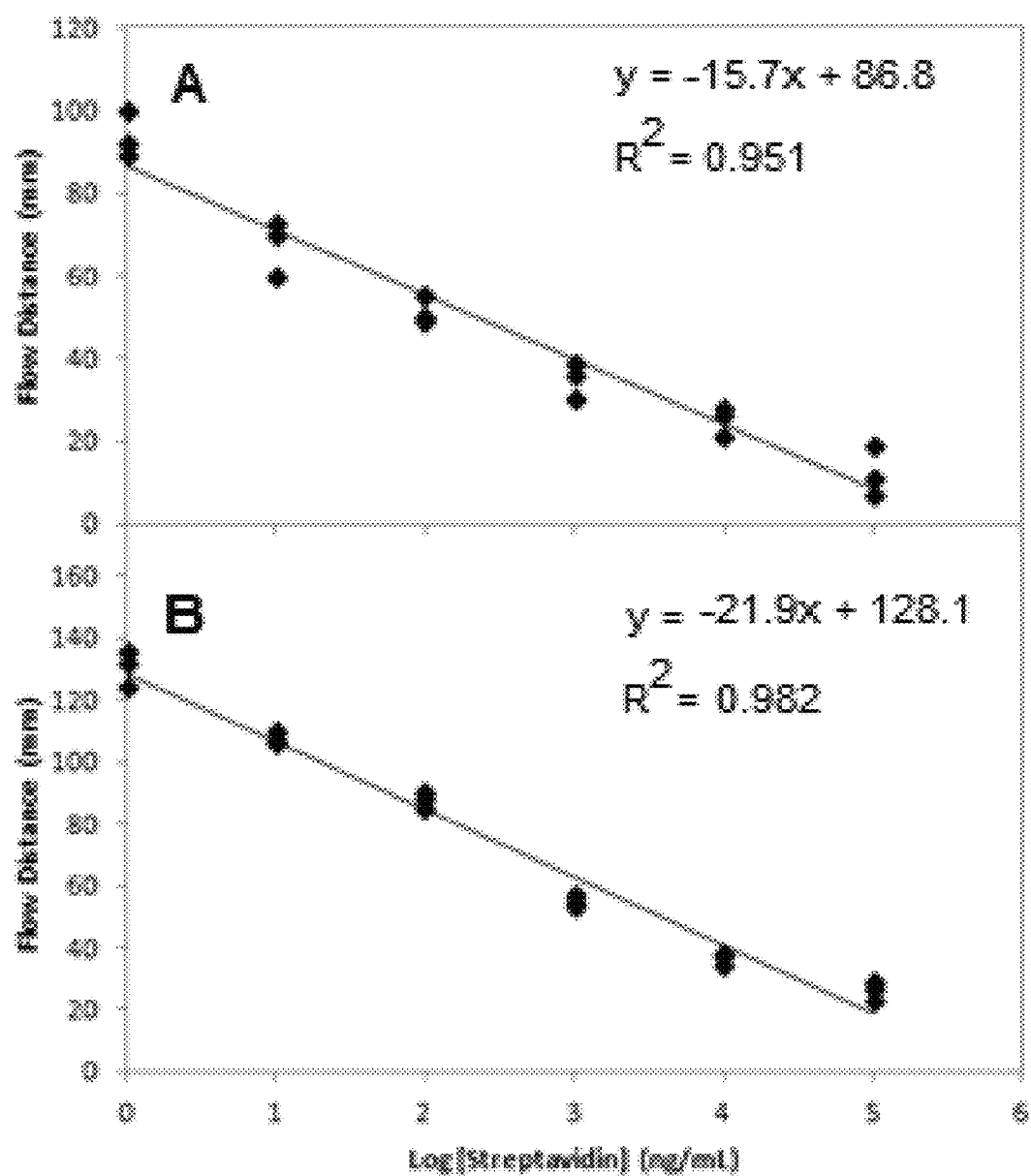
FIG. 5. Flow distance traveled as a function of streptavidin concentration in biotin-modified microchannels (58 μm wide) of two different heights, with a 0.5 mm thick PDMS top layer. (A) 13 μm deep channels. (B) 17 μm deep channels.

The correlation was explored between flow distance and streptavidin concentration for two different channel heights. A plot of flow distance for various streptavidin solution concentrations in biotin-modified 13 µm tall channels is given in FIG. 5A. The plot shows a linear relationship between the logarithm of streptavidin concentration and flow distance, along with a good $R^2$ value of 0.95. A different set of experiments was carried out on biotin-modified 17 µm tall channels (FIG. 5B) and likewise showed a linear relationship with an improved $R^2$ value of 0.98 and less data scatter than in the 13 µm tall channels. Also, improved assay sensitivity was observed for deeper versus shallower channels, with a 40% increase in the magnitude of the calibration curve slope. The linear relationship between logarithm of streptavidin concentration and flow distance across a broad swath of concentrations in different channel heights highlights the wide dynamic range for this method. The lowest quantified streptavidin concentration was 1.0 ng/mL, with flow distances of ~100 mm for 13 µm tall channels and ~130 mm for 17 µm tall channels, with potential to detect lower streptavidin concentrations using longer channels. This very low detection limit compared to the ~0.2 µg/mL protein detection limits in paper-based assays[17, 23] and excellent quantitation capability marks an important improvement in performance for simple, rapid and inexpensive assays.

Several plausible explanations were evaluated and eliminated for the observed flow behaviors that do not involve channel constriction. Measured were contact angles of solutions of different streptavidin concentrations (1 ng/mL-100 µg/mL) on b-BSA coated PDMS to be 25-26°. Thus, the mechanism of flow stoppage is clearly not linked to concentration-dependent changes in surface wettability or tension. In addition, flow experiments on buffer solutions lacking streptavidin were performed in 13 µm tall b-BSA coated PDMS microchannels with 0.45 and 0.5 mm cover layers. These solutions flowed the entire channel length, indicating that the flow stoppage was not due to any pressure drop or channel constriction caused by capillary action. In addition, flow is unaffected by non-specific adsorption, as streptavidin solutions from 1 ng/mL-100 µg/mL) in 13 µm tall channels coated with BSA (lacking biotin) flowed the entire channel distance. Thus non-specific adsorption, which is a significant problem for conventional immunoassays, appears not to play a major role in the flow valve devices, showing promising potential for extension to other assay systems.

Further explored was the mechanism of flow stoppage via channel closure using fluorescent imaging. After capillary flow of a solution containing streptavidin mixed with the unreactive small molecule marker fluorescein in a b-BSA-coated channel, the fluorescence in the first 10 mm of the microchannel was imaged to observe any differences due to constriction (FIG. 6A-B). Plots of normalized fluorescence signal across the channel at different flow distances demonstrate a significant, 3-fold increase in channel fluorescence (i.e., cross-sectional area) moving away from the solution introduction point until the signal plateaus at around 6 mm flow distance, as shown in FIG. 6C. Importantly, control experiments wherein streptavidin was replaced by BSA and similarly flowed with fluorescein (FIG. 6D-F) showed no appreciable change in channel cross-section over the same portion of the flow channel, clearly supporting a channel constriction mechanism that is specific to biotin-streptavidin interaction. It is hypothesized that once this initial portion of the channel is constricted to a sufficiently small aperture, flow stops. Thus, the capillary flow distance of the target solution depends on the time needed to close the first few millimeters of channel enough for flow to cease, which will be a function of target concentration. Hence, for future "flow valve" designs, only the first few millimeters of the channel need to be modified with receptor, and deeper channels after the constriction zone could also be used in designing assays without serpentine channels.

Receptors must recognize at least two distinct sites on the target to crosslink channels. Streptavidin readily meets this criterion with four biotin binding sites. Polyclonal antibodies or two different monoclonal antibodies to a target would recognize different epitopes and should also cause receptor-mediated crosslinking of microchannels in response to an antigen target. Additionally, hybridization of a target nucleic acid sequence to complementary surface-attached single-stranded oligonucleotides should mediate microchannel closure. Are antigen-antibody or base pairing interactions strong enough to develop "flow valve" assays? The unbinding forces for target-receptor pairs have been studied by scanning probe microscopy, and were 200-300 pN[25, 26] per biotin-streptavidin molecular pair. The measured unbinding force for a single antigen-antibody pair is 50-60 pN,[27-29] which is less than biotin-streptavidin by a small factor of 3-6 that could likely be accommodated through adjusting device parameters. The unbinding force for hybridized DNA oligonucleotides, depending on the sequence and number of base pairs, ranges from 450 pN[30] for 14-mer sequences to 2700 pN for 20-base-long hybridized pairs.[31] These published unbinding data affirm the likely feasibility of generalization of "flow valve" systems beyond biotin-streptavidin measurements to nucleic acid hybridization and antigen-antibody interactions.

Figure 6:
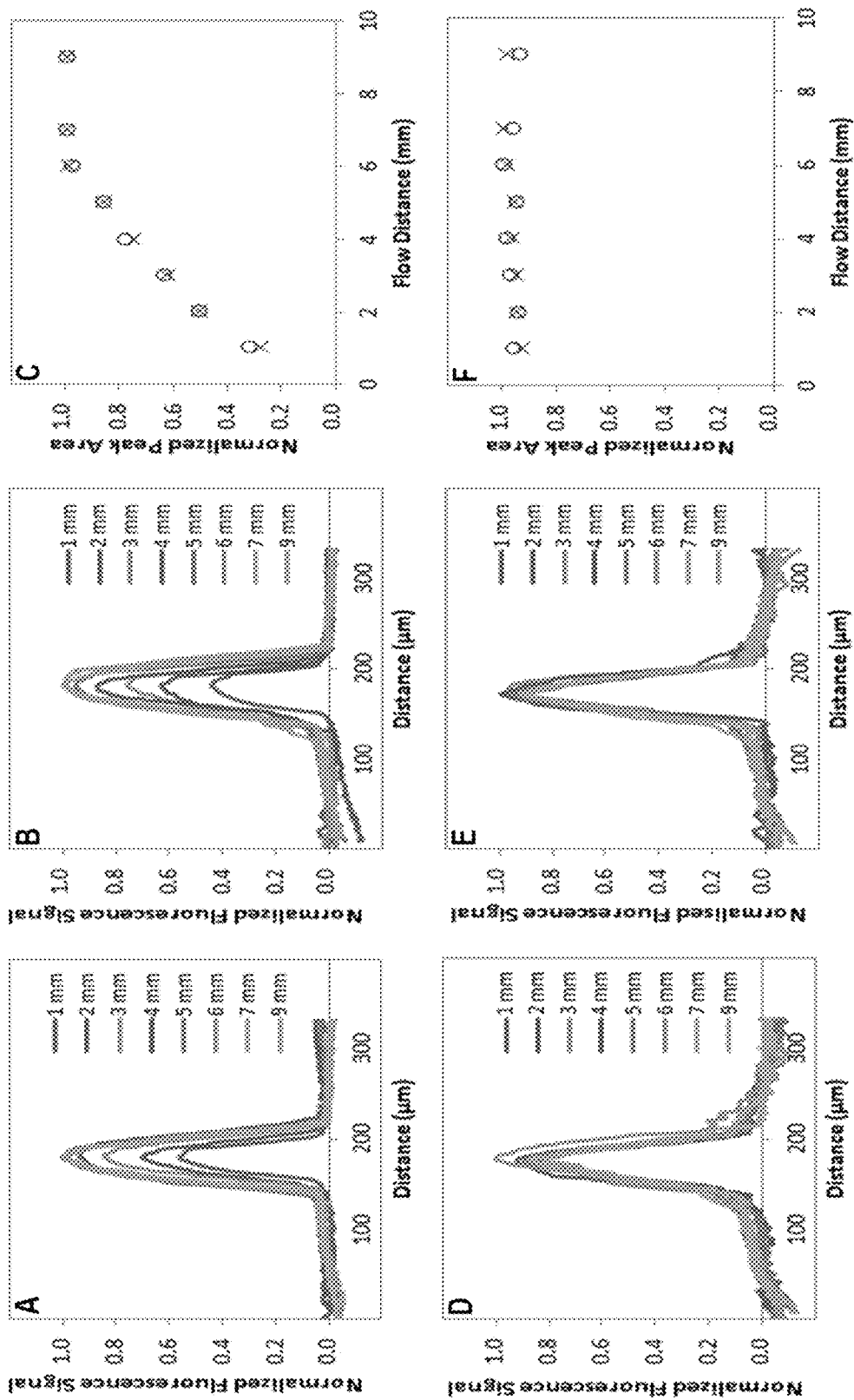
FIG. 6. Plots of background subtracted, normalized fluorescence signal and peak area in 13 μm deep biotin-modified channels as a function of channel position and flow distance to probe constriction. (A-B) Unlabeled streptavidin (500 μg/mL) mixed with fluorescein sodium salt (80 ng/mL); signal (which scales with pathlength or channel height) is lowest near the reservoir, rising gradually to a constant level at about 6 mm flow distance. (C) Normalized peak area of unlabeled streptavidin versus flow distance is lowest near the reservoir, rising gradually to a constant level at about 6 mm flow distance. (D-E) Unlabeled BSA (500 μg/mL) mixed with fluorescein sodium salt (80 ng/mL); signal is essentially constant along the flow distance. (F) Normalized peak area of unlabeled BSA versus flow distance is approximately constant throughout the flow distance.

A key question regarding flow valve assays is the following: how can molecular-scale (~10 nm) surface interactions translate into much larger, micrometer-dimension alterations in microchannel diameter that can affect flow? It is believed that the answer can be found in the data in FIG. 6, coupled with the posited channel constriction mechanism illustrated at the bottom of FIG. 1. At the edges of the microchannels, where the curved regions meet the flatter bottom segment (see FIG. 1), the channel height is at or near the ~10 nm molecular scale, such that biotin-streptavidin crosslinking of the top surface to the bottom is possible. This interaction would pull the top and bottom surfaces incrementally closer, enabling similar molecular-scale crosslinking to occur moving inward toward the middle of the channel. As this interaction progresses, the edges of the channel would be constricted, while the middle would remain open (i.e., FIG. 1J-K). Importantly, the data in FIG. 6A-B are indicative of exactly this type of change in cross-sectional channel profile induced by streptavidin solution flow, strongly supporting the hypothesized mechanism. In further support of surface intermolecular interactions leading to channel constriction, some simple force calculations were made. A typical surface density of b-BSA molecules is $6 \times 10^{16}/m^2$,[24] while the force needed to unbind one biotin-streptavidin molecular pair has been measured as 200-300 pN.[25, 26] Hence, the force per area exerted by biotin-streptavidin surface interactions would be $1.2 \times 10^7$ N/m$^2$, or 1740 psi, which is at least a factor of 100 greater than the 5-10 psi needed to completely close similarly shaped PDMS microfluidic valves.[21] Thus, it is concluded that molecular-scale interactions have sufficient force to induce channel constriction and that the occurrence of such interactions from the edges toward the centers of these microchannels is both plausible and consistent with the channel imaging data that was obtained.

Conclusions

Demonstrated is a detectorless microfluidic approach for quantifying target analytes through simple visual inspection of capillary flow distance in a microchannel. Identified and characterized are three important parameters (solution viscosity, PDMS cover layer thickness and channel height) that affect the flow distance in these assays for the biotin-streptavidin model system. In addition, found was a linear relationship between flow distance in biotin-modified channels and logarithm of streptavidin concentration over a 100,000-fold range of concentrations. Moreover, identified and studied is a plausible mechanism of channel constriction and how this leads to concentration-dependent flow distances. Importantly, streptavidin concentrations were measured as low as 1 ng/mL using these microsystems, demonstrating low detection limits, with potential for future improvement. "Flow valve" microfluidic devices show great promise for simplified, low cost, but high performance chemical analysis that could be extended to antigen and nucleic acid determinations. "Flow valve" systems are especially promising for POC testing due to their portability, and detectorless and label-free quantitation.

Example II

Microdevices were constructed essentially as in Example I, except the receptors were antibodies attached to the PDMS surface by a silanization technique where the PDMS was modified with 3-glycidoxytrimethoxypropylsilane (COPS), to which antibodies were attached by reacting the COPS epoxy end groups with amine groups on antibodies. The microdevices were tested, and concentration of the target was determined by measurement of the distance of sample flow along the channel after a predetermined time.

Example III

Microdevices are constructed essentially as in Example II, except the receptors are amine-modified nucleic acids that are reacted with the GOPS-silanized PDMS surface.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

| Table of References |
|---|
| 1. LaCourse, W. R. Anal. Chem. 2002, 74, 2813-2831. |
| 2. Svec, F. J. Chromatogr. A 2010, 1217, 902-924. |
| 3. Li, Y.; Lee, M. L. J. Sep. Sci. 2009, 32, 3369-3378. |
| 4. Jorgenson, J. W. Annu. Rev. Anal. Chem. 2010, 3, 129-150. |
| 5. Aebersold, R.; Goodlett, D. R. Chem. Rev. 2001, 101, 269-295. |
| 6. Griffiths, W. J.; Wang, Y. Chem. Soc. Rev. 2009, 38, 1882-1896. |
| 7. Perry, R. H.; Cooks, R. G.; Noll, R. J. Mass. Spectrom. Rev. 2008, 27, 661-699. |
| 8. Harris, G. A.; Galhena, A. S.; Fernandez, F. M. Anal. Chem. 2011, 83, 4508-4538 |
| 9. Gillie, J. K.; Hochlowski, J.; Arbuckle-Keil, G. A. Anal. Chem. 2000, 72, 71R-79R |
| 10. Mulvaney, S. P.; Keating, C. D. Anal. Chem. 2000, 72, 145R-157R. |
| 11. Kaplan, L. A.; Pesce, A. J., Clinical Chemistry: Theory, Analysis, Correlation. 5th ed.; Elsevier: Amsterdam, 2010. |
| 12. Zhang, H.; Wang, S.; Fang, G. J. Immunol. Meth. 2011, 368, 1-23. |
| 13. Vashist, S. K.; Zheng, D.; Al-Rubeaan, K.; Luong, J. H. T.; Sheu, F.-S. Anal. Chim. Acta 2011, 703, 124-136. |
| 14. Tomlinson, C.; Marshall, J.; Ellis, J. E. Curr. Med. Res. Opin. 2008, 24, 1645-1649 |
| 15. Martinez, A.W.; Phillips, S. T.; Butte, M. J.; Whitesides, G. M. Angew. Chem. Int. Ed. 2007, 46, 1318-1320. |
| 16. Dungchai, W.; Chailapakul, O.; Henry, C. S. Analyst 2011, 136, 77-82. |
| 17. Liu, H.; Crooks, R. M. J. Am. Chem. Soc. 2011, 133, 17564-17566. |
| 18. Zhong, M.; Lee, C. Y.; Croushore, C. A.; Sweedler, J. V. Lab Chip 2012, 12, 2037-2045 |
| 19. Barber, J. P.; Lunt, E. J.; George, Z. A.; Yin, D.; Schmidt, H.; Hawkins, A. R. IEEE Phot. Technol. Lett. 2006, 18, 28-30. |
| 20. Duffy, D. C.; McDonald, J. C.; Schueller, O. J. A.; Whitesides, G. M. Anal. Chem. 1998, 70, 4974-4984. |
| 21. Unger, M. A.; Chou, H.-P.; Thorsen, T.; Scherer, A.; Quake, S. R. Science 2000, 288, 113-116. |
| 22. Sheely, M. L. Indust. Eng. Chem. 1932, 24, 1060-1064. |

-continued

Table of References

23. Martinez, A. W.; Phillips, S. T.; Butte, M. J.; Whitesides, G. M. Angew. Chem. Int. Ed. 2007, 46, 1318-1320.
24. Sun, Y. S.; Landry, J. P.; Fei, Y. Y.; Zhu, X. D. Anal. Chem. 2009, 81, 5373-5380
25. Wong, S. S.; Joselevich, E.; Woolley, A. T.; Cheung, C. L; Lieber, C. M. Nature 1998, 394, 52-55.
26. Moy, V. T.; Florin, E.-L; Gaub, H. E. Science 1994, 266, 257-259.
27. Allen, S.; Chen, X.; Davies, J.; Davies, M. C.; Dawkes, A. C.; Edwards, J. C.; Roberts, C. J.; Sefton, J.; Tendler, S. J. B.; Williams, P. M. Biochemistry 1997, 36, 7457-7463.
28. Ros, R.; Schwesinger, F.; Anselmetti, D.; Kubon, M.; Schafer, R.; Pluckthun, A.; Tiefenauer, L. Proc. Natl. Acad. Sci. USA 1998, 95, 7402-7405.
29. Harada, Y.; Kuroda, M.; Ishida, A. Langmuir 2000, 16, 708-715.
30. Noy, A.; Vezenov, D. V.; Kayyem, J. F.; Meade, T. J.; Lieber, C. M. Chem. Biol. 1997, 4, 519-527.
31. Mazzola, L. T.; Frank, C. W.; Fodor, S. P. A.; Mosher, C.; Lartius, R.; Henderson, E. Biophys. J. 1999, 76, 2922-2933.

What is claimed is:

1. A fluidic device for measuring concentration of a target in solution comprising:
a microchannel in a material, the microchannel having an inlet at a first end;
at least the portion of the walls of the microchannel near the first end coated with a receptor,
the receptor reactive with the target to form a cross-linked coating;
the material at at least the first end of a deformable material, and
the microchannel at at least the first end having a geometric cross-section,
the cross-section and the deformable material such that the microchannel is deformable and constrictable by a progressing crosslinking between opposing wall surfaces where crosslinking between opposing wall surfaces deforms the microchannel to constrict the microchannel until closure of the microchannel to provide a concentration flow valve effect where flow distance of the solution in the microchannel until closure depends on concentration of the target;
the microchannel and material having properties to show visual contrast between a portion of the microchannel filled with solution, and a portions of the microchannel not filled with solution.

2. A fluidic device for measuring concentration of a target in solution comprising:
a microchannel in a material, the microchannel having an inlet at a first end;
at least the portion of the walls of the microchannel near the first end coated with a receptor,
the receptor reactive with the target to form a cross-linked coating;
the material at at least the first end of a deformable material, and
the microchannel at at least the first end having a geometric cross-section,
the cross-section and the deformable material such that target-mediated crosslinking of receptors on opposing surfaces of the microchannel deform the cross-section to make capillary flow distance of solution in the microchannel dependent on target concentration;
the microchannel and material having properties to show visual contrast between a portion of the microchannel filled with solution, and a portions of the microchannel not filled with solution.

3. The device of claim 2 wherein the cross-section of the microchannel at the first end is a geometric shape with at least two acute angles.

4. The device of claim 2 wherein the cross-section of the microchannel at the first end is semicircular.

5. The device of claim 2 wherein the device comprises one or more micropattern calibration markings for measuring length of the microchannel filled with solution.

6. The device of claim 2 wherein the deformable material comprises an elastomer.

7. The device of claim 2 wherein the deformable material comprises polydimethylsiloxane.

8. The device of claim 7 wherein the polydimethylsiloxane above the channel has a thickness between 0.4-1.0 mm.

9. The device of claim 2 wherein the deformable material comprises a fluoroelastomer.

10. The device of claim 2 wherein channel height is between 1 and 50 microns.

11. The device of claim 2 wherein channel height is between 5 and 20 microns.

12. The device of claim 2 wherein the channel length is between 10 and 1000 mm.

13. The device of claim 2 wherein the channel length is between 20 and 200 mm.

14. The device of claim 1 wherein receptor can react with at least two sites on the target.

15. A method of detecting the concentration of a target in a solution comprising:
directing a solution containing the target into the inlet of a microchannel,
at least the portion of the walls of the microchannel near the first end coated with a receptor,
the receptor reactive with the target to form a cross-linked coating;
the microchannel cross-section at at least the first end having a geometric cross-section and of a deformable material such that the microchannel is deformable and constrictable by product of target-mediated crosslinking of the receptor and target on adjacent surfaces;
continuing flow of the solution into the microchannel as the crosslinked product of the receptor and product forms in the channel and deforms and constricts the channel to provide a concentration flow valve effect where capillary flow distance of solution in the microchannel depends on target concentration;
measuring the concentration of the target in the solution by visually observing and
measuring length of the portion of the microchannel filled with solution.

16. The method of claim 15 wherein the concentration is measured after the flow of the solution has stopped or is insignificant.

17. The method of claim 15 wherein the concentration is measured after a predetermined time of flow.

18. The method of claim 15 where viscosity of the sample is between 1 and 4 cP.

19. The method of claim 15 wherein receptor can react with at least two sites on the target.

* * * * *